United States Patent [19]
DeVoe et al.

[11] Patent Number: 5,118,559
[45] Date of Patent: Jun. 2, 1992

[54] FLUORESCENT DEGREE OF CURE MONITORS

[75] Inventors: Robert J. DeVoe, St. Paul; Katherine A. Brown-Wensley, Lake Elmo; George V. D. Tiers, St. Paul, all of Minn.

[73] Assignee: Minnesota Mining and Manufacturing Company, St. Paul, Minn.

[21] Appl. No.: 709,719

[22] Filed: Jun. 3, 1991

Related U.S. Application Data

[62] Division of Ser. No. 359,108, May 31, 1989, Pat. No. 5,047,444.

[51] Int. Cl.$^5$ .................... B32B 7/00; B32B 27/00; D04H 1/00; D04H 3/00
[52] U.S. Cl. ................................ 428/262; 428/264; 428/266; 428/290; 428/265; 428/267; 428/268; 428/447; 428/500; 428/511; 428/515; 428/516
[58] Field of Search ............... 522/99, 100, 103, 182, 522/65, 70; 526/93, 103, 284, 280, 256, 259, 268, 279; 528/15, 25, 27, 28; 428/262, 264, 266, 290

[56] References Cited

U.S. PATENT DOCUMENTS

| | | | |
|---|---|---|---|
| 3,019,336 | 1/1962 | Johns | 250/43.5 |
| 3,091,651 | 5/1963 | Soderquist et al. | 260/668 |
| 3,091,652 | 5/1963 | Soderquist et al. | 260/668 |
| 3,118,060 | 1/1964 | Klein | 250/71 |
| 3,130,303 | 4/1964 | Dobbins | 250/43.5 |
| 3,341,010 | 9/1967 | Switzer | 209/111.5 |
| 3,546,165 | 12/1970 | Morgan | 260/47 |
| 3,547,827 | 12/1970 | Switzer | 252/301.2 |
| 3,577,885 | 5/1971 | Wells | 73/150 |
| 3,675,015 | 7/1972 | Geib | 250/71 R |
| 3,871,885 | 3/1975 | Hertler | 96/35.1 |
| 3,912,928 | 10/1975 | Rush et al. | 250/302 |
| 3,930,063 | 12/1975 | Miller et al. | 427/54 |
| 3,956,630 | 5/1976 | Mellows | 250/302 |
| 3,965,350 | 6/1976 | Molina | 250/302 |
| 3,968,083 | 7/1976 | Quinn | 428/287 |
| 4,009,151 | 2/1977 | Pearson | 526/284 |
| 4,013,623 | 3/1977 | Turner | 526/284 |
| 4,025,710 | 5/1977 | Stolka et al. | 526/284 |
| 4,058,732 | 11/1977 | Wieder | 250/461 B |
| 4,109,152 | 8/1978 | Aoki et al. | 250/486 |
| 4,152,723 | 5/1979 | McMahon et al. | 358/106 |
| 4,250,382 | 2/1981 | Libby | 250/302 |
| 4,395,496 | 7/1983 | Wittmann et al. | 522/99 |
| 4,454,295 | 6/1984 | Wittmann et al. | 522/99 |
| 4,508,884 | 4/1985 | Wittmann et al. | 522/99 |
| 4,536,654 | 8/1985 | Vaerman | 250/458.1 |
| 4,599,155 | 7/1986 | Suzuki et al. | 522/99 |
| 4,618,566 | 10/1986 | Guillet et al. | 526/284 |
| 4,621,193 | 11/1986 | Van Hoye | 250/302 |
| 4,651,011 | 3/1987 | Ors et al. | 250/459.1 |
| 4,684,678 | 8/1987 | Schultz et al. | 523/466 |
| 4,741,860 | 5/1988 | Hartman | 252/301.21 |
| 4,755,684 | 7/1988 | Leiner et al. | 250/461.1 |
| 4,922,113 | 5/1990 | Melancon | 250/372 |
| 4,978,731 | 12/1990 | Melancon | 528/15 |

FOREIGN PATENT DOCUMENTS

| | | |
|---|---|---|
| 1370783 | 10/1974 | United Kingdom . |
| 1422526 | 1/1976 | United Kingdom . |
| 2016370 | 9/1979 | United Kingdom . |
| 2194244 | 3/1988 | United Kingdom . |

OTHER PUBLICATIONS

Wang, F. W., et al., Polymer (1984), 25, 690.
Loutfy, R. O., "Photophysical and Photochemical Tools in Polymer Science: Conformation, Dynamics, Morphology", Boston (1986) p. 429.
Dickenson, P., et al., Polymer Preprints (1988) 29, 530–531.
DeSilva, et al., Analytical Chemistry, 48:1, Jan. 1976.
Radio Shack Dictionary of Electronics, Tandy, TX (1974) p. 632.
Ferrand Optical Co., May 1957.
Thommes et al., Talanta 7, pp. 181–186 (1961).
Yu, W. C., et al., Polymer Preprints (1988) 29, 532–533.
Helv. Chim. Acta (1977), 60, 1073.
J. Org. Chem. (1987) 52, 688.
Ber. (1906), 39, 3062.
Stegemeyer, H., Ber. Bunsenges Phys. Chem. (1968), 72, 335–340.
White, et al., Fluorescence Analysis, Marcell Dekker, Inc. NY (1970) pp. 200–209.
Jones, et al., IBM Technical Disclosure Bulletin, 27:4A, Sep. 1984, p. 2202.
U.S. Ser. No. 07/220,991.

Primary Examiner—Marion E. McCamish
Assistant Examiner—Susan Berman
Attorney, Agent, or Firm—Gary L. Griswold; Walter N. Kirn; Lorraine R. Sherman

[57] ABSTRACT

A curable composition, the cure of which can be monitored optically, comprises at least one of a hydride curable silicone, an ethylenically unsaturated compound, and a cationically polymerizable monomer, and as cure monitor dibenzofulvene or derivatives thereof. The cure monitor is a latent fluorophore which reacts under the cure conditions to form a UV-detectable fluorophore.

The invention also provides a method for measuring degree of cure of a polymeric material which can be a coating or an article.

16 Claims, No Drawings

FLUORESCENT DEGREE OF CURE MONITORS

This is a division of application no. 07/359,108 filed May 31, 1989, now U.S. Pat. No. 5,047,444 issued Sept. 10, 1991.

FIELD OF THE INVENTION

This invention relates to curable and cured compositions containing compounds useful in, and a method for, non-destructive determination of the extent of cure of a polymer. The method is particularly suitable for on-line manufacturing processes wherein polymer films or coatings are cured, for example, in adhesive tapes, release liners, protective coatings, and printed circuit boards.

BACKGROUND OF THE INVENTION

In an increasingly competitive environment, industry is looking for ways to improve product reliability and quality, maximize efficiency to reduce costs of their manufacturing processes, and reduce product inventory. Such objectives are critically dependent upon the accurate and rapid measurement of product properties, which in many applications depends upon uniform and reproducible curing of polymers. In particular, abrasion and solvent resistance of protective coatings is diminished when a coating is incompletely cured. Similarly, performance of pressure sensitive adhesives and release coatings is particularly sensitive to incomplete and non-uniform cure.

Traditional processes of measuring extent of cure generally rely upon off-line methods, including non-destructive methods such as infrared or UV-visible absorption spectroscopy, and destructive methods such as solvent extraction, thermal analysis (glass transition temperature), and surface tack (for example ASTM-D1640-83).

A non-destructive, on-line process for monitoring degree of cure, recently disclosed in U.S. Pat. No. 4,651,011, teaches a method wherein a fluorescent material such as a dye is dissolved in a monomer, oligomer, or polymer and can be used to monitor the degree of cure or polymerization via fluorescence anisotropy or polarization by means of an optical inspection system.

Other methods of following degree of cure by means of fluorescence spectroscopy utilize probe molecules such as those described in (a) F. W. Wang, R. E. Lowry, W. H. Grant, *Polymer* (1984), 25, 690; (b) R. O. Loutfy in "Photophysical and Photochemical Tools in Polymer Science: Conformation, Dynamics, Morphology", NATO ASI Series, Series C, Vol. 182, M. A. Winnik, Ed., Reidel: Boston (1986) pp. 429–448; and (c) Dickinson, C. S. P. Sung, *Polymer Preprints* (1988), 29, 530–531; W. C. Yu, X. Y. Huang, C. S. P. Sung, *Polymer Preprints* (1988), 29, 532–533.

The Wang, Loutfy and U.S. Pat. No. 4,651,011 (Ors and Scarlata) methods of monitoring extent of cure require use of soluble probe molecules which are not covalently bound to the resulting polymer, providing potential environmental and measurement problems with probe "bloom".

The Wang and Loutfy methods have been shown to be useful as cure monitors only at low viscosity (less than 300 cP, reference (b) above). The Sung method requires use of special fluorescent crosslinking agents.

As to the curatives themselves, many dibenzofulvene derivatives are known in the art, as in U.S. Pat. Nos. 3,091,651 and 3,091,652, *Helv. Chim. Acta* (1977), 60, 1073; *J. Org. Chem.* (1987), 52, 688; and *Ber.* (1906), 39, 3062. Furthermore, it is known that certain dibenzofulvenes are either non-fluorescent or weakly fluorescent (H. Stegemeyer, *Ber. Bunsenges. Phys. Chem.* (1968), 72, 335–340).

SUMMARY OF THE INVENTION

The present invention provides novel curable compositions and a method of measuring the degree of cure and all permutations of order of mixing of above materials, and (b) exposing the resulting polymerized composition to radiant energy of a wavelength range centered around $\lambda_1$, (c) measuring uvescence intensity at a wavelength range centered around $80_2$ emitted by said composition during or after polymerization to provide an indication of degree of cure, using for example, a photomultiplier, a photodiode or a phototube.

There is also provided a method for measuring degree of cure of a coated article, comprising the steps of:

(a) applying the polymerizable mixture as described above to a substrate by methods known in the art, such as bar or knife coater, reverse roll, knurled roll, or spin coatings, or by dipping, spraying, brushing, and the like, with or without a coating solvent, (b) optionally allowing the solvent to evaporate, (c) allowing the mixture to polymerize or adding energy to the mixture to effect polymerization and provide a composition comprising a uvaphore that absorbs radiant energy of a wavelength centered around $\lambda_1$, and emits radiant energy of a wavelength centered around $\lambda_2$. $\lambda_1$ and $\lambda_2$ each being a wavelength in the ultraviolet portion of the electromagnetic spectrum, and the mean of the range of $\lambda_1$ being below the mean of the range of $\lambda_2$, and (d) exposing said resulting polymerized composition to radiant energy at $\lambda_1$, (e) measuring uvescence intensity at $\lambda_2$ during or after polymerization to provide an indication of degree of cure of the coated article.

In a further aspect, there is provided a polymerizable composition comprising:

(a) at least one of a hydride curable silicone and an ethylenically unsaturated monomer, optionally a polymerization promoter, optionally solvent, and (b) a dibenzofulvene or derivative thereof as polymerization inhibitor.

In a still further aspect, the polymerized composition just described is provided.

As used in this application:

"hydride curable silicone" means a curable mixture of silicones which comprises an ethylenically unsaturated siloxane and a polyhydrosiloxane, as described, for example, in U.S. Pat. No. 4,504,645;

"cationically polymerizable monomer" means a monomer or oligomer such as vinyl ethers, 1,2-, 1,3-, and 1,4-cyclic ethers, ethylenically unsaturated hydrocarbons, N-vinyl compounds, cyclic formals, and cyclic organosiloxanes;

"ethylenically unsaturated monomer or compound" means those monomers or oligomers that polymerize by a free radical reaction;

"uvescence" means fluorescent or phosphorescent emission in the ultraviolet portion of the spectrum, i.e., in the range of 250 to 400 nm, preferably 270 to 350 nm, more preferably 300 to 335 nm; more particularly it means emission of a photon from a substance occurring as a result of a spin conserving transition from an electronic excited state to a lower electronic state; the practice of fluorescence spectroscopy is described, for example, in J. R. Lakowicz, "Principles of Fluorescence Spectroscopy," Plenum Press: New York, 1983;

"uvaphore" means a material which is uvescent;, more particularly it means a uvescent group, compound, or substance which on absorption of radiation in the ultraviolet portion of the spectrum (i.e., 200 to 400 nm, preferably 250 to 350 nm) emits ultraviolet radiation and differs from luminescent compounds of the prior art which emit light in the visible portion of the spectrum above about 400 nm;

"latent uvaphore" means a material which is substantially non-uvescent, but which can be converted via a chemical reaction to a material which is uvescent;

"non-uvescent" material or "substantially non-uvescent" material means a material which exhibits a uvescence quantum yield that is less than half, preferably less than 20%, more preferably less than 10% the uvescence quantum yield of the corresponding uvaphore at the measurement wavelength;

"catalyst", "initiator", and "polymerization promoter" are terms which are used interchangeably and which mean a material which is added to a curable composition to effect cure at a rate that is faster than it would be in the absence of the catalyst;

"polymerization" and "cure" are terms which are used interchangeably, and mean that one or more chemical reactions resulting in an increase in molecular weight have occurred in a monomer, oligomer, or polymer, or mixtures thereof;

"spectroscopically detectable amount" means a quantity such that if an equal number of moles of 9-ethylfluorene is substituted for the latent uvaphore, 9-ethylfluorene uvescence can be observed in a conventional (commercially available) fluorescence spectrometer;

"bloom" means that an additive material separates from a polymeric coating in which the material was molecularly dispersed, and appears on the external surface of the coating surface, normally as an opaque or semi-opaque solid deposit, but occasionally as an oily or sticky film;

"probe molecule" means a molecule which when present in a polymeric or pre-polymeric system, confers upon the composition a detectable sensitivity to changes in its physical or chemical nature; for the purposes of this invention, the term will be limited to molecules which can be detected by non-destructive optical means such as by use of photosensitive or spectroscopic instruments as is known by those skilled in the art, preferably usable of compositions such as hydride curable silicones, ethylenically unsaturated compounds, and cationically polymerizable compounds, incorporating a latent uvaphore that is converted during cure to a uvaphore, which can be used on-line, and which can be polymer-bound, thereby obviating environmental and measurement problems of "bloom". In another aspect of the invention, the latent uvaphore can additionally function as an inhibitor for certain polymerization catalysts, preventing polymerization from occurring until desired.

Briefly, the present invention provides a curable composition, the cure of which can be monitored optically in the UV, comprising at least one of a hydride curable silicone, an ethylenically unsaturated compound, and a cationically polymerizable monomer, and as cure monitor dibenzofulvene or derivatives thereof. The cure monitor is a latent uvaphore which reacts under cure conditions to form a uvaphore which preferably is polymer-bound.

In another aspect, the invention provides a method for measuring degree of cure of a polymeric material comprising the steps of:

(a) polymerizing a mixture comprising a polymerizable composition comprising at least one of a hydride curable silicone, an ethylenically unsaturated monomer or oligomer, and a cationically polymerizable monomer or oligomer, optionally a polymerization promoter, optionally a solvent, and a spectroscopically detectable amount of a latent uvaphore comprising at least one of dibenzofulvene and dibenzofulvene derivatives, in the presence of added energy when required, to provide an at least partially polymerized composition comprising a uvaphore that absorbs radiant energy of a wavelength centered around $\lambda_1$ and emits radiant energy of a wavelength centered around $\lambda_2$, $\lambda_1$ and $\lambda_2$ each being a wavelength in the ultraviolet portion of the electromagnetic spectrum, and the mean of the range of $\lambda_1$ being below the mean of the range of $\lambda_2$, on-line and more preferably involving uvescence in the ultraviolet spectrum, and sensitive to degree of cure or polymerization; and "added energy" means at least one of thermal, actinic, or electron beam energy.

DETAILED DESCRIPTION OF THE INVENTION

Dibenzofulvene derivatives in the methods and compositions of this invention are compounds having the following general formula I:

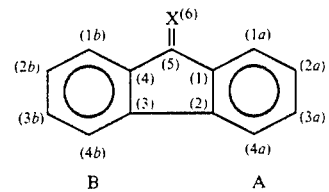

wherein X can be $CR^1R^2$, an oxygen atom, or $NR^1$, wherein $R^1$ and $R^2$ independently each represent a hydrogen atom, alkyl, aryl, alkenyl, aralkenyl, alkynyl, aralkynyl, alkaryl or aralkyl group, or $R^1$ and $R^2$ together represent a cyclic or polycyclic hydrocarbyl group of ring sizes 3 to 12 atoms, all of which can include up to 50 carbon atoms and 0 to 30 heteroatoms such as unitary nonperoxidic oxygen, nitrogen, silicon or sulfur. Each aromatic ring designated A and B in formula I (hereafter referred to as benzo groups) can be substituted with up to four, preferably zero to three, substituents, preferably none of which are in the 1a or 1b positions on the benzo rings, and which are chosen from 1) alkyl, aryl, aralkyl, alkaryl, acyl, acylamido, amino, hydroxycarbonyl, alkoxycarbonyl, alkoxy, aryloxy groups of up to 50 carbon atoms and 0 to 30 unitary fluoro, chloro, bromo, nitrogen, silicon, sulfur, and nonperoxidic oxygen atoms, 2) cyano groups, bromo, chloro, and fluoro atoms, and 3) silyl and siloxy groups containing up to 200 silicon atoms and up to 200 unitary nitrogen, sulfur, and nonperoxidic oxygen atoms, (such groups preferably being chosen so as to improve solubility), or benzo groups A and B may together or each independently be single rings or part of a fused aromatic ring system having 1 to 4 rings such as naphthalene, phenanthrene, anthracene, pyrene, and the like, and A and B together or each independently may contain up to two ring nitrogen atoms.

The latent uvaphore may be added to the curable composition at a level of 0.001% to 10% by weight, preferably 0.005% to 5% by weight, most preferably 0.01% to 1.0% by weight of the solids content of the composition. It is desirable that the level of latent uvaphore is sufficient to provide a spectroscopically detectable amount of uvaphore. The uvaphore is a minor component of the polymerized composition and is present in an amount such that the uvescence intensity is that produced by no more than 5 weight percent, preferably no more than 1 weight percent of 9-ethylfluorene, but in any case the uvaphore is present in an amount at least equivalent in uvescence intensity to 0.001 weight percent, preferably 0.01 weight percent, of 9-ethylfluorene.

Amount or intensity of uvescence from the composition upon excitation is a measure of the conversion of I to II (Reaction 1 below), in that I is non-uvescent or substantially non-uvescent and II is uvescent. X is as defined above. Y and Z represent addends in a cure reaction; for example, Y and Z may be chosen from H- and $-SiR^3$ wherein $R^3$ represents a group or groups covalently bonded to Si such that $HSiR^3$ represents a polyhydrosiloxane in the curing of hydride curable silicones, or Y and Z each may represent chain atoms in the backbone of the cured composition (polymer). When the rate of conversion of I to II is comparable to, preferably slightly slower than, the rate of the curing reaction, intensity of uvescence from the composition is a measure of the extent of cure.

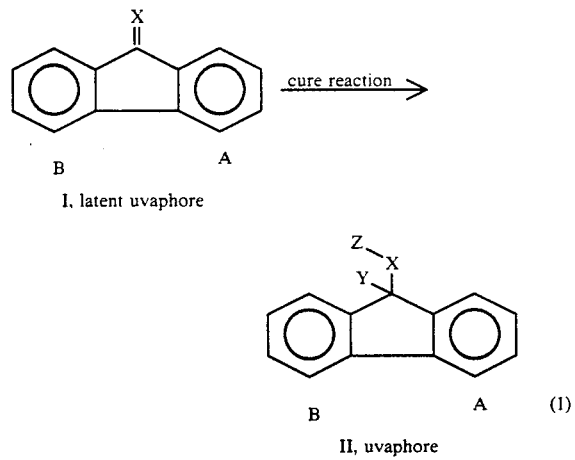

I, latent uvaphore

II, uvaphore    (1)

In another aspect, the present invention allows for the continuous on-line monitoring of degree of cure of a variety of polymers, with the following advantages. The latent uvaphore molecule becomes a uvaphore which can be covalently bound to the polymer during the cure reaction, avoiding the problem of bloom, a particularly sensitive area in adhesives and release coatings. For example, if the addend Y or Z in Reaction (1) is a moiety on a polymer, such as a silicon in a polyhydrosiloxane portion of a hydride curable silicone, uvaphore II will be covalently bound to the polymer. The probe is a "positive response" probe, meaning that the measured signal (uvescence intensity) increases as curing proceeds. Wavelength response of uvaphores formed from preferred latent uvaphores is such that the uvaphores absorb strongly at the primary mercury lamp output (254 nm) but not in the solar spectrum, and uvesces at a wavelength measurably different from that of typical potential interfering substances: emission maxima of reacted dibenzofulvenes II are variously from 300 to 400 nm, and preferably 300 to 350 nm, while fluorescent brighteners and film bases (aromatic polyesters, polyurethanes, epoxies, etc.) often fluoresce in a range above 300 and up to 550 nm, permitting choice of a reacted dibenzofulvene II for which the emission differs measurably from all potential interference. A further advantage of this invention is the lack of visible fluorescence (or color) to degrade the appearance of the coating.

The uvaphore can be covalently bound either in the polymer backbone or as a pendant polymer group or it can be dispersed or dissolved in the polymerized mixture.

In yet another aspect of the invention, the dibenzofulvenes can be used in certain polymerizable compositions or formulations to moderate cure rate. In such formulations, inhibitors are used to moderate curing at room temperature, allowing adequate potlife for coating, molding, and other processing while allowing adequate cure rates at elevated temperatures. In free radical (e.g., ethylenically unsaturated compounds) and in hydride curable silicone compositions, dibenzofulvenes of the present invention act as moderate polymerization inhibitors, providing adequate potlife for processing while allowing adequate cure rates at elevated temperature or upon exposure to actinic or electron beam radiation for radiation sensitive compounds. Extent to which cure rates are modified is affected by such factors as structure and/or concentration of dibenzofulvene or derivative thereof, catalyst, and other inhibitors; temperature; and order and timing of mixing of various components in the curable composition. In particular, any modification of catalyst chemical composition or activity as a result of any variation in order or conditions of mixing of catalyst, dibenzofulvene, and other components of the curable composition, as may be apparent to those skilled in the art, is included within the scope of this invention.

Polymerizable compositions of this invention can include coatings on articles, solutions, films, adhesives, articles, and the like. Coating compositions can be applied to substrates or supports including any solid surface, for example, paper, cardboard, wood, cork, plastics such as polyester, polyurethane, polyamide, polycarbonate, polyolefin, etc., woven and nonwoven fabric such as cotton, polyester, polyolefin, nylon, etc., metals such as aluminum, iron, etc., glass, fused silica, ceramics, etc., including fabrics made therefrom. Substrates which are continuous webs or fibers are particularly amenable to the process of the invention and may be inspected "on-line" to permit continuous control of the process variables. Polymerizable compositions of this invention may contain plasticizers, fillers, pigments, and the like, used in amounts suitable for their intended purposes, as is well known to those skilled in the art.

Compositions of the instant invention may be prevented from polymerization until desired by protecting as necessary, e.g., from actinic radiation, or from heat (as by refrigerated storage), when retention of the curable compositions well beyond the useful potlife is desired.

Dibenzofulvenes of the present invention are synthesized by methods known in the art, including (a) the Wittig reaction, (b) base catalyzed condensation of fluorene derivatives with aldehydes and ketones, (c) dechlorination or dehydrochlorination of acid chlorides, (d) reaction of titanocene alkylidene compounds with 9-fluorenone derivatives, and (e) methods taught in U.S. Pat. Nos. 3,091,651 and 3,091,652.

Synthesis of dibenzofulvenes by the Wittig reaction is carried out by mixing an ylide of formula III, below, and an aldehyde or ketone of general formula IV, below, in an inert solvent, thereby forming a solution or a suspension (for general reviews of the Wittig reaction see "Advanced Organic Chemistry," Third Edition, J. March, Wiley: New York, 1985, pp. 845-854, and references therein). In formulae III and IV, benzo groups A and B and groups $R^1$ and $R^2$ are as defined above. Solvents may be chlorinated solvents such as methylene chloride, carbon tetrachloride, or chloroform; ethers such as tetrahydrofuran, diethyl ether, methyl tert-butyl ether; aromatic solvents such as benzene, toluene, or xylene; aliphatic and cycloaliphatic solvents such as cyclohexane, methylcyclohexane, heptane, or hexane; and mixtures thereof. In some cases it may be advantageous to use up to a ten-fold molar excess of either reagent III or IV. The mixture is stirred under an inert atmosphere for 0.1 to 200 hours at a temperature of $-78°$ to 200° C., preferably 0.1 to 72 hours at 0° to 70° C. The reaction product is separated from the mixture by filtration through an adsorbent such as silica gel or alumina, evaporation of the solvent, and optionally recrystallization of the residual product from liquids such as ethyl alcohol, methyl alcohol, hexane, heptane, pentane or low boiling petroleum ether, chlorocarbons such as methylene chloride, chloroform, and carbon tetrachloride, aromatic liquids such as benzene, toluene, and xylene, and mixtures of solvents; or sublimation of the material, preferably under vacuum.

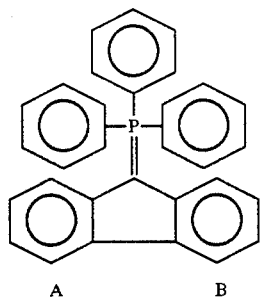

III

A      B (e.g., fluorenylidene-triphenylphosphorane)

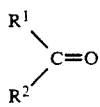

IV

Alternatively, the Wittig reaction may be carried out by mixing an ylide of formula Va or formula Vb with a 9-fluorenone derivative VI, and proceeding as above.

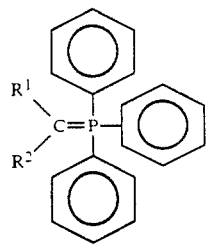

Va (alkylidenetriphenylphosphorane)

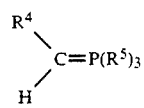

Vb alkylidenetrialkylphosphorane

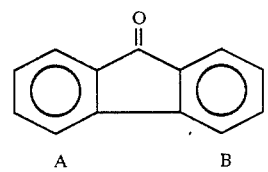

VI

A      B (9-fluorenone)

Benzo groups A and B and groups $R^1$ and $R^2$ are as defined above, $R^4$ can be hydrogen or methyl, $R^5$ can be methyl or ethyl.

Ylides of structures III, Va and Vb are known in the art. For example, fluorenylidenetriphenylphosphorane has been prepared as described in J. Am. Chem. Soc. 1947, 69, 723, and is commercially available from Lancaster Synthesis Ltd., Morecambe, England, and general methods of preparing ylides such as III, Va and Vb from the corresponding alkyltriarylphosphonium halides are discussed in "Advanced Organic Chemistry," Third Edition, J. March, Wiley: New York, 1985, pp. 845-854, and references therein.

Suitable ylides of general structure III are fluorenylidenetriphenylphosphorane, (2-chlorofluorenylidene)triphenylphosphorane, (4-azafluorenylidene)triphenylphosphorane, (2-bromofluorenylidene)triphenylphosphorane, (1-methylfluorenylidene)triphenylphosphorane, and (1-methoxycarbonylfluorenylidene)triphenylphosphorane.

Suitable aldehydes of general structure IV include acetaldehyde, propionaldehyde, isobutyraldehyde, 10-undecenal, heptaldehyde, 2-ethylhexaldehyde, benzaldehyde, 4-chlorobenzaldehyde, 4-methoxybenzaldehyde, and acrolein.

Ketones of general structure IV which can be useful in some embodiments of the invention include acetone, 2-butanone, cyclohexanone, cyclopentanone, cycloheptanone, benzophenone, acetophenone, propiophenone, butyrophenone, and valerophenone.

Suitable ylides of general structure Va and Vb are, for example, methylidenetriphenylphosphorane, methylidenetrimethylphosphorane, ethylidenetriethylphosphorane, benzylidenetriphenylphosphorane, isobutylidenetriphenylphosphorane, 1-hexylidenetriphenylphosphorane, and (1-undec-10-enylidene)triphenylphosphorane.

Suitable 9-fluorenones of the general structure VI are, for example, 9-fluorenone, 2-methyl-9-fluorenone, 1-chloro-9-fluorenone, 2-bromo-9 fluorenone, 2-cyano-9-fluorenone, 4-chloro-9-fluorenone, 3-chloro-9-fluorenone, 2,7-dichloro-9-fluorenone, 4-chloro-2-methyl-9-fluorenone, 2-dimethylamino-9-fluorenone, 2,4,7-trichloro-9-fluorenone, 2,7-dibromo-9-fluorenone, and the like.

Alternatively, dibenzofulvenes of this invention can be prepared by base catalyzed condensation of a fluorene derivative of structure VII (below) and an aldehyde or ketone of structure IV, as described, for example, in *Liebigs Ann. Chem.* (1906), 347, 296. In structure VII, benzo groups A and B are as defined above.

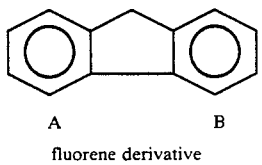

VII fluorene derivative

Suitable fluorene derivatives of general structure VII include fluorene, 4-methylfluorene, 4-azafluorene, 1-chlorofluorene, 2-bromofluorene, 2-fluorenecarboxylic acid, methyl 4-fluorenecarboxylate, 3-chlorofluorene, 4,5-methylenephenanthrene, 2,7-dichlorofluorene, 2,4,7-trichlorofluorene, 4-chloro-2-methylfluorene, and 2-cyanofluorene.

Alternatively, dibenzofulvenes of this invention can be prepared by reaction of 9-fluorenones of the general structure VI with titanocene alkylidene compounds as described in K. A. Brown-Wensley, S. L. Buchwald, L. Cannizzo, L. Clawson, S. Ho, D. Meinhardt, J. R. Stille, D. Straus, and R. H. Grubbs, *Pure & Appl. Chem.* (1983), 55, 1733.

Dibenzofulvene itself, formula I (X=CH$_2$), is known, and can be prepared as is described in U.S. Pat. Nos. 3,091,651 and 3,091,652, or as is described in *Helv. Chim. Acta* (1977), 60, 1073. Alternatively, dibenzofulvenes of structure I with X=CH$_2$ can be prepared from 9-fluorenylmethyl chloroformates of structure VIII (below) by treatment with a mild base such as trialkylamine, as described in Example 2, below.

9-Fluorenylmethyl chloroformates are prepared as described in U.S. Pat. Nos. 3,835,175 and 3,906,031. To a solution of a fluorenylmethyl chloroformate of general structure VIII, below, wherein A and B are as defined above, in an inert solvent, e.g., chlorinated solvents such as methylene chloride, carbon tetrachloride, chloroform, ethers such as tetrahydrofuran, diethyl ether, methyl tert-butyl ether, aromatic solvents such as benzene, toluene, xylene, aliphatic and cycloaliphatic solvents such as cyclohexane, methylcyclohexane, heptane, hexane, and mixtures thereof, is added a solution of a trialkylamine in a solvent of the same group while maintaining the temperature between 30° C. and 75° C. After gas evolution has ceased, the mixture is filtered, solvent is evaporated from the filtrate, and the crude dibenzofulvene derivative is distilled at reduced pressure as is disclosed in U.S Pat. Nos. 3,091,651 and 3,091,652, or isolated by addition of aqueous alkali solution (e.g., 1 to 10 weight percent sodium hydroxide or potassium hydroxide) to the filtered reaction mixture, separation and drying of the organic layer with a drying agent, e.g., anhydrous magnesium sulfate, calcium chloride, or sodium sulfate, filtration, and evaporation of the solvent to provide the desired product.

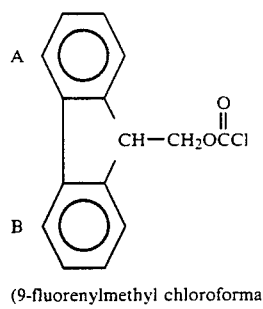

VIII (9-fluorenylmethyl chloroformate)

Representative 9-fluorenylmethyl chloroformates include 9-fluorenylmethyl chloroformate, 9-(4-methyl)-fluorenylmethyl chloroformate, 9-(4-aza)fluorenylmethyl chloroformate, 9-(1-chloro)fluorenylmethyl chloroformate, 9-(2-bromo)fluorenylmethyl chloroformate, 9-(3-chloro)fluorenylmethyl chloroformate, 9-(2,7-dichloro)fluorenylmethyl chloroformate, 9-(2,4,7-trichloro)fluorenylmethyl chloroformate, 9-(4-chloro-2 methyl)fluorenylmethyl chloroformate, 9-(cyano)-fluorenylmethyl chloroformate, 9-(4-COOCH$_3$)-fluorenylmethyl chloroformate, 9-(2-COOH)fluorenylmethyl chloroformate, etc.

The same method can be used if 9-fluorenylmethyl chloroformates are replaced with N-(9-fluorenylmethoxycarbonyloxy)succinimide or 9-fluorenylmethyl pentafluorophenyl carbonate, available from Aldrich Chemical Co., Milwaukee, Wis.

Preferred dibenzofulvenes include dibenzofulvene (formula I wherein X=CH$_2$), 6-methyldibenzofulvene [formula I wherein X=CH(CH$_3$)], 6-vinyldibenzofulvene [formula I wherein X=CH(CH=CH$_2$)], 6-ethyldibenzofulvene [formula I wherein X=CH(C$_2$H$_5$)], 6-isopropyldibenzofulvene [formula I wherein X=CHCH(CH$_3$)$_2$], 6-hexyldibenzofulvene [formula I wherein X=CH(n-C$_6$H$_{13}$)], and 9-fluorenone (formula I wherein X= oxygen).

Useful hydride curable silicones include those mentioned in U.S. Pat. No. 4,504,645 which are incorporated herein by reference. Specific ethylenically-unsaturated silicon compounds may contain as few as one silicon atom, such as vinyltriethoxylsilane, or more than one silicon atom, such as vinylpentamethyldisiloxane, 1,3-divinyltetramethyldisiloxane, 1,1,3-trivinyltrimethyldisiloxane, 1,1,3,3-tetravinyldimethyldisiloxane, or polysiloxane precursors, as well as high molecular weight polysiloxanes containing up to 10,000 or more silicon atoms per molecule and having a molecular weight in the range of 150 to 10,000,000, preferably 200 to 2,000,000. Among cyclic materials, tetramethyltetrallylcyclotetrasiloxane, and tetramethyltetravinylcyclotetrasiloxane are included. Preferred compounds are vinyldimethyl endblocked polydimethylsiloxane fluids of 50 to 20,000 cP, most preferably 200 to 5,000 cP. Also preferred are vinyldimethyl endblocked polydimethylsiloxane fluids with up to 50 percent, preferably up to 20 percent, by weight of the dimethylsiloxy units replaced by diphenylsiloxy or methylphenylsiloxy units. Also included within the scope of ethylenically-unsaturated polysiloxanes are cyclic compounds containing silicon-bonded vinyl or allyl radicals, such as the cyclic trimer, tetramer, or pentamer of methylvinylsiloxane [(CH$_2$=CH)(CH$_3$)SiO]$_3$, or methylallylsiloxane,

[(CH$_2$=CH—CH$_2$)(CH$_3$)SiO)]$_w$, wherein subscript w is an integer of 3 to 10.

Polyhydrosiloxanes useful in the present invention include 1,3-dimethyldisiloxane, 1,1,3,3-tetramethyldisiloxane, as well as high polymers containing up to 10,000 or more silicon atoms per molecule including hydrogen siloxane units (HSiO$_{1.5}$), methylhydrogen siloxane units (HSiCH$_3$O), dimethylhydrogen siloxane units [HSi(CH$_3$)$_2$O$_{0.5}$], and dihydrogen siloxane units (H$_2$SiO), such as (CH$_3$)$_3$SiO[Si(CH$_3$)(H)Si(CH$_3$)$_3$. Also included are cyclic materials such as cyclic polymers of methyl hydrogen siloxane having the formula (CH$_3$SiHO)$_w$, wherein subscript w in an integer from 3 to 10, such as 1,3,5,7-tetramethylcyclotetrasiloxane.

Useful ethylenically unsaturated compounds include monomers such as mono-, di-, or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethylacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyl-dimethylmethane, bis[1-(3-acryloxy-2-hydroxy)]-p-propoxyphenyldimethylmethane, tris(2-acryloxyethyl)isocyanurate trimethacrylate; the bis-acrylates and bis-methacrylates of polyethylene glycols of molecular weight 200-500, copolymerizable mixtures of acrylated monomers such as those of U.S. Pat. No. 4,652,274, and acrylated oligomers such as those of U.S. Pat. No. 4,642,126; unsaturated amides such as acrylamide, methylene bis-acrylamide, methylene bis-methacrylamide, 1,6-hexamethylene bis-acrylamide, diethylene triamine tris-acrylamide and beta-methacrylaminoethyl methacrylate; and vinyl compounds such as styrene, divinylbenzene diallyl phthalate, divinyl succinate, divinyl adipate, divinyl phthalate, and vinyl azlactones as disclosed in U.S Pat. No 4,304,705. Mixtures of two or more monomers can be used if desired.

Useful cationically polymerizable compounds include 1,2-, 1,3-, and 1,4-cyclic ethers (also designated as 1,2-, 1,3-, and 1,4-epoxides), vinyl ethers, N-vinyl compounds, ethylenically unsaturated hydrocarbons, cyclic formals, and cyclic organosiloxanes. An extensive list of cationically polymerizable monomers which can be used in this invention are given in U.S. Pat. Nos. 3,347,676 and 3,842,019.

Cyclic ethers which can be polymerized in accordance with this invention include those described in "Ring-Opening Polymerizations", Vol. 2, by Frisch and Reegan, Marcel Dekker, Inc (1969). Suitable 1,2-cyclic ethers are monomeric and polymeric types of epoxides. They can be aliphatic, cycloaliphatic, aromatic, or heterocyclic and will typically have an epoxy equivalency of from 1 to 6, preferably 1 to 3. Particularly useful are aliphatic, cycloaliphatic, and glycidyl ether type 1,2-epoxides such as propylene oxide, epichlorohydrin, styrene oxide, vinylcyclohexene oxide, vinylcyclohexene dioxide, glycidol, butadiene oxide, diglycidyl ether of bisphenol A, 3,4-epoxycyclohexylmethyl3,4-epoxycyclohexanecarboxylate, 3,4-epoxy-6-methylcyclohexylmethyl-3,4-epoxy-6-methylcyclohexanecarboxylate, bis(3,4-epoxy-6-methylcyclohexylmethyl) adipate, dicyclopentadiene dioxide, epoxidized polybutadiene, 1,4-butanediol diglycidyl ether. polyglycidyl ether of phenol-formaldehyde resole or novolak resin, resorcinol diglycidyl ether, and epoxy silicones, e.g., dimethylsiloxanes having cycloaliphatic epoxide or glycidyl ether groups. Bireactive monomers such as glycidyl methacrylate are also useful. A wide variety of commercial epoxy resins are available and listed in "Handbook of Epoxy Resins" by Lee and Neville, McGraw Hill Book Company, New York (1967) and in "Epoxy Resin Technology" by P. F. Bruins, John Wiley & Sons, New York (1968). Representative of 1,3- and 1,4-cyclic ethers which can be polymerized in accordance with this invention are oxetane, 3,3-bis(chloromethyl)oxetane, and tetrahydrofuran.

Another useful class of cationically-sensitive monomers which can be polymerized in accordance with this invention is represented by the general formula:

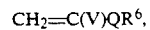

$CH_2=C(V)QR^6$, wherein Q is —O—or —NR$^7$— (where R$^7$ is hydrogen or lower alkyl of 1 to 4 carbon atoms), R$^6$ is hydrocarbyl, hydrocarbylcarbonyl, halohydrocarbyl, or hydroxyhydrocarbyl which can contain up to 50 carbon atoms and up to 25 halo, nonperoxidic oxygen, or hydroxyl groups when Q is oxygen, or R$^6$ is hydrocarbyl, hydrocarbylcarbonyl, or hydrocarbylsulfonyl when Q is nitrogen, and V is hydrogen, or an alkyl, aryl, or other hydrocarbyl group having up to 50 carbon atoms, or R$^6$ (as hydrocarbylcarbonyl) and R$^7$ can be connected to form a 5-or 6-membered cyclic structure containing nitrogen and carbon as ring atoms. The term "hydrocarbyl" is used herein in its usual sense to mean alkyl, alkenyl, aryl, cycloalkyl, cycloalkenyl, alkaryl, arylalkyl, and the like. In general, monomers of this type contain a vinyl group and are typified by vinyl alkyl ethers, such as vinyl methyl ether, vinyl ethyl ether, vinyl n-butyl ether, vinyl 2-chloroethyl ether, vinyl isobutyl ether, vinyl phenyl ether and vinyl 2-ethylhexyl ether, vinyl ethers of substituted aliphatic alcohols such as 1,4-di(ethenoxy)butane, vinyl 4-hydroxy-butyl ether, and N-vinyl compounds such- as N-vinyl-N-methyl octanesulfonamide and N-vinylpyrrolidone. A description of vinyl monomers and their use in preparing polymers is set forth in "Vinyl and Related Polymers," by Schildknecht, published by John Wiley & Sons, Inc., New York (1952).

Other cationically-sensitive monomers which can be polymerized in this invention include ethylenically unsaturated hydrocarbons such as isobutylene; dienes such as 1,3-butadiene and isoprene; styrene, 4-vinyltoluene, and divinylbenzene; cyclic formals such as trioxane, 1,3-dioxolane, 2-vinyl-1,3-dioxolane and 2-methyl-1,3-dioxolane; and cyclic siloxanes which can contain various groups attached to a silicon atom such as a hydrocarbon radical (alkyl, aryl, aralkyl, alkaryl), an alkenyl hydrocarbon radical (vinyl, allyl or acryloyloxy-alkyl), a halogenated hydrocarbon radical, a carboxy-containing hydrocarbon radical or ester group, a cyanohydrocarbon radical, all of which can contain up to 50 carbon atoms or hydrogen, halogen or a hydroxy group.

Representative cationically sensitive cyclic siloxanes are hexamethylcyclotrisiloxane, octamethylcyclotetrasiloxane, phenylheptamethylcyclotetrasiloxane, vinylheptamethylcyclotetrasiloxane, methacryloyloxymethylheptamethylcyclotetrasiloxane, 2-bromoethylheptamethylcyclotetrasiloxane, 3-chloropropylheptamethylcyclotetrasiloxane, 1,3,5-tri(3,3,3-trifluoropropyl)- trimethylcyclotrisiloxane, acetoxymethylheptamethylcyclotetrasiloxane, cyanomethylheptamethylcyclotetrasiloxane, 1,3,5-trihydrotrimethylcyclotrisiloxane, and chloroheptamethylcyclotetrasiloxane. Other known cyclic siloxanes are listed in "Chemistry and Technology of Silicones" by Walter Noll, Academic Press, New York (1968), Tables 41, 44 and 45. Many of these monomers are commercially available.

Cationically sensitive cyclic siloxanes can also be polymerized in the presence of relatively low molecular weight linear siloxanes such as hexamethyldisiloxane, chloropentamethyldisiloxane and octamethyltrisiloxane which serve to terminate the growing chain and provide stable fluids or fluids having reactive end groups.

There is a host of commercially available cationically-sensitive monomers which can be used in this invention many of which can be designated by trademarks which are indicated below in quotation marks. In particular, cyclic ethers which are readily available include propylene oxide, oxetane, epichlorohydrin, tetrahydrofuran, styrene oxide, vinylcyclohexene oxide, glycidol, glycidyl methacrylate, octylene oxide, phenyl glycidyl ether, 1,2-butene oxide, diglycidyl ether of bisphenol A (e.g., "Epon 828" and "DER 331"), vinylcyclohexene dioxide (e.g., "ERL-4206"), 3,4-epoxycyclohexylmethyl-3,4-epoxycyclohexanecarboxylate (e.g., "ERL-4221"), 3,4-epoxy-6-methylcyclohexylmethyl 3,4-epoxy-6-methylcyclohexanecarboxylate (e.g., "ERL-4201"), bis(3,4-epoxy-6-methylcyclohexylmethyl)adipate (e.g., "ERL-4289"), aliphatic epoxy modified with polypropylene glycol (e.g., "ERL-4050" and "ERL-4052"), dipentene dioxide (e.g., "ERL-4269"), epoxidized polybutadiene (e.g., "Oxiron 2001"), silicone epoxy (e.g., "Syl-Kem 90"), 1,4-butanediol diglycidyl ether (e.g., Araldite RD-2), polyglycidyl ether of phenolformaldehyde novolak (e.g., "DER-431", "Epi-Rez 521" and "DER-438", resourcinol diglycidyl ether (e.g., "Kopoxite"), polyglycol diepoxide (e.g., "DER 736"), polyacrylate epoxide (e.g., "Epocryl U-14"), urethane modified epoxide (e.g., "QX3599"), polyfunctional flexible epoxides (e.g., "Flexibilizer 151"), and mixtures thereof as well as mixtures thereof with curing agents, co-curatives, or hardeners which also are well known (see Lee and Neville and Bruins, supra). Representative of the co-curatives or hardeners which can be used are acid anhydrides such as nadic methyl anhydride, cyclopentanetetracarboxylic dianhydride, pyromellitic dianhydride, cis-1,2-cyclohexanedicarboxylic anhydride, and mixtures therof.

Adjuvants such as fillers, plasticizers, flowing agents, colorants, pigments, and the like can be added in effective amounts for their intended purposes so long as the adjuvant does not interfere with polymerization of the composition or uvescence thereof.

Curable compositions as described above may be cured with the aid of at least one of ionizing radiation, heat, and electromagnetic radiation, and there can be employed thermally or photochemically activated catalysts or initiators as known to those skilled in the art. Catalysts or initiators can be used in amounts in the range of 0.001 to 10 weight percent, preferably 0.005 to 5 weight percent, of the polymerizable compositions. Cured compositions are useful as release coatings, adhesives, protective coatings, sealants, biocompatible coatings, binders for magnetic media and abrasives, and the like.

Curable compositions containing dibenzofulvene or a dibenzofulvene derivative exhibit a positive response, that is, an increase in uvescence intensity as cure proceeds. Since there may be some detectable uvescence signal in uncured materials (due to the monomer or substrate on which the curable composition is coated, additives, or the latent uvaphore, or impurities therein) and since the rate of growth of uvescence may vary as the latent uvaphore, catalyst, monomer, inhibitor, and other additives are varied (either by varying the chemical structure or concentration), as well as varying with process parameters, it may be preferred to measure uvescence in the uncured composition as well as in the composition at one or more stages of cure. Use of such data to construct calibration curves or to measure absolute or relative uvescence measurements so as to determine extent of cure, is well-known to those skilled in the art.

Objects and advantages of this invention are further illustrated by the following examples, but the particular materials and amounts thereof recited in these examples, as well as other conditions and details, should not be construed to unduly limit this invention.

In the following examples, Me designates methyl, infrared (IR) spectra were obtained on a Perkin-Elmer 983 Infrared Spectrometer (Perkin-Elmer, Norwalk, Connecticut), fluorescence spectra were obtained on a Perkin-Elmer MPF-44B Fluorescence Spectrometer or a Spex Industries Fluorolog TM 2 F112XI fluorescence spectrometer (Spex Industries, Edison, NJ), and ultraviolet (UV)-visible absorption spectra were obtained on a Perkin-Elmer 330 spectrophotometer.

EXAMPLE 1

This example demonstrates synthesis of 6-methyldibenzofulvene (formula I, X = CHCH$_3$).

A mixture of 1.06 g 9-fluorenylidenetriphenylphosphorane (Aldrich Chemical Company, Milwaukee, Wisconsin), 0.5 g acetaldehyde, and 10 g methylene chloride was stirred under nitrogen at room temperature overnight. Workup (according to the method described by R. M. Boden, *Synthesis* 1975, 784) consisted of evaporating solvent on a rotary evaporator, digesting the resulting solid in 100-150 ml pentane, filtering the pentane solution through silica gel on a fritted filter, and evaporating the filtrate to yield 0.40 g of 6-methyldibenzofulvene m.p. 102–103° C., which was identified by proton nmr, IR, and UV-visible spectroscopies. Compounds 6-(n-hexyl)dibenzofulvene formula I, X =CH(n-hexyl)]and 6-(iso-butyl)dibenzofulvene [formula I, X TM CH(iso-butyl)] were synthesized similarly.

EXAMPLE 2

This example illustrates synthesis of dibenzofulvene (formula I, X=CH$_2$).

To a solution of 5.08 g of 9-fluorenylmethyl chloroformate (Aldrich Chemical Company) in 20 ml methylene chloride cooled in a dry ice/acetone bath was added dropwise a solution of 8 ml triethylamine in 7 ml methylene chloride. The mixture was stirred for 45 minutes and allowed to warm to room temperature. Methylene chloride and excess triethylamine were removed at reduced pressure (no heating) to yield an off white solid. This solid was heated under vacuum (ca. 0.1 mm Hg) until it vaporized, by means of a heat gun, and the distillate was collected (3.00 g white solid, poly(dibenzofulvene), 86%), leaving 2.8 g triethylammonium chloride (100%). The polydibenzofulvene was cracked (depolymerized) in a sublimator at 0.08 mm Hg (using a heat gun) to yield 2.50 g (71% yield) light yellow solid soluble in halogenated hydrocarbons, identified by proton nmr as dibenzofulvene.

Dibenzofulvene spontaneously polymerized on standing at room temperature (about 24 hours) or on heating, but was readily stored for extended periods of time as either the homopolymer or at low temperature (<0° C.) as the monomer. The polymer can be easily and quantitatively cracked to dibenzofulvene by heating in vacuo (see U.S. Pat. Nos. 3,091,651 and 3,091,652).

EXAMPLE 3

This example demonstrates the synthesis of 6-vinyl-dibenzofulvene (formula I, X=CH—CH=CH$_2$). A mixture of 3.0 g fluorenylidenetriphenylphosphorane, 0.56 g acrolein, and 30 ml methylene chloride was stirred at room temperature under nitrogen for 24 hours. Solvent was evaporated under reduced pressure and the residue was successively digested in four portions of pentane. The combined pentane solutions were filtered through 5 cm of silica gel in a column of 2 cm diameter, then the silica gel was washed with 300 ml more pentane. The combined pentane filtrate was evaporated under reduced pressure to yield 0.65 g (46% yield) light yellow crystalline solid, mp 64.5–65.5° C. Proton nmr (400 MHz) showed pure 6-vinyl-dibenzofulvene. The yield is expected to be higher if more of the volatile acrolein is used.

EXAMPLE 4

This example illustrates the increase in uvescence intensity in a composition containing a latent uvaphore and a polyhydrosiloxane. A solution of 6-methyldibenzofulvene (compound I, X=CHCH$_3$) $7.3 \times 10^6$ M in heptane was prepared and 3 ml was placed in a 1.0 cm path length quartz (silica) cuvette. Approximately 0.4 g of polyhydrosiloxane of approximate formula, HSi(MSiMe$_2$—OiMe$_2$H wherein Me=methyl and 0.1 ml $8 \times 10^4$ M platinum catalyst solution (1% by weight of bis(-divinyltetramethyldisiloxane)platinum(0) in vinyl-terminated polydimethylsiloxane; see U.S. Pat. No. 3,715,334) were added to the cuvette. The UV-visible spectrum was taken before and after heat treatment. A fluorescence spectrum (excitation wavelength 254 nm, emission wavelength scanned from 270–400 nm) was taken before and at regular intervals during the heat treatment. Heating was accomplished by placing the cuvette in a hot water bath at 80–90° C., and removing the cuvette to record fluorescence spectra. The sample was substantially non-uvescent before heating. Uvescence with a maximum intensity at 304 nm increased with time at 80–90° C., reaching an intensity approximately 400 times that of the initial intensity at 304 nm. Uvescence was essentially the same as that of fluorene derivatives (described in S. L. Murov, "Handbook of Photochemistry", Marcel Dekker, New York, 1973). Changes in the UV-visible absorption spectrum were also indicative of a conversion of methyldibenzofulvene to a fluorene chromophore (absorption maximum at 270 to 280 nm), such as formula II.

EXAMPLE 5

This example illustrates the increase in uvescence intensity in a composition containing a latent uvaphore and an ethylenically unsaturated monomer.

A solution of 0.0137 g dibenzofulvene (formula I, X=CH$_2$), 0.01 g 2,2′-azobis(isobutyronitrile) (AIBN), 1.0 g hexanediol diacrylate. and 1.0 g chloroform was prepared. coated onto polypropylene film and air dried. A polypropylene cover film was placed over the coating and the fluorescence spectrum obtained (excitation wavelength =254 nm, emission wavelength scanned from 270 to 400 nm). The sample was then placed in an oven at 100° C.; the sample was removed periodically to monitor the fluorescence spectrum. A new uvescence band with emission maxima at 304 and 318 nm appeared and grew with time, reaching a value that was 6 times more intense (at 318 nm) than that of the original spectrum after 9 minutes at 100° C. and 25 times more intense after 20 minutes. The film was non-tacky and hard to the touch after 5 to 9 minutes at 100° C., indicating that curing had occurred.

EXAMPLE 6

This example demonstrates the growth in uvescence intensity in a composition containing a latent uvaphore and an epoxy monomer.

A solution of 1.0 g ERL-4221 (Union Carbide, Danbury, CT), 0.016 g dibenzofulvene (formula I, X TM CH$_2$), 0.3 g chloroform, and 0.04 g 10% SbF$_5$/diethylaniline (U.S. Pat. No. 4,503,211) in gamma-butyrolactone was coated onto polypropylene and allowed to air dry. A cover sheet of polypropylene was placed over the tacky coating, the sample was heated and uvescence was monitored as in Example 5. The film was nontacky and hard to the touch after ca. 2 minutes at 100° C., while uvescence at 304 and 318 nm increased with time, reaching values that were 2 times and 25 times the initial intensity at 318 nm in 2 and 31 minutes, respectively.

EXAMPLE 7

This example describes a curable silicone composition containing dibenzofulvene as latent uvaphore; curing and analyzing the composition to correlate extent of cure and uvescence intensity.

To 2.59 g of ethylenically unsaturated polydimethylsiloxane of approximate formula (CH$_2$=CH)Me$_2$-Si(OSiMeOSiMe$_2$(CH=CH$_2$) was added 0.013 g of maleate inhibitor (see U.S. Pat. No. 4,533,575), then 0.023 g of dibenzofulvene (formula I, X =CH$_2$) in 2 g of chloroform, then 0.027 g of Pt(0) catalyst (the solution as described in Example 4) and then 0.067 g of polyhydrosiloxane of approximate formula Me$_3$SiOSiMe(H-)OSiMe$_3$ (Dow Corning DC-1107 TM) Chloroform was then removed under vacuum, to produce a translucent curable silicone composition containing latent uvaphore. The mixture was placed between two sheets of polypropylene, and the uvescence spectrum monitored as a function of time at 100° C as in Example 5. In addition, an independent measurement of the degree of cure was made at each point by infrared spectroscopy on the same sample. The infrared spectroscopy method quantitatively measures absorption of the Si-H band at 2170 cm$^{-1}$ versus a peak at 1950 cm$^{-1}$ (which does not change and functions as an internal standard). From these data, one can calculate how much of the Si-H, which hydrosilates vinyl groups in the silicone composition to effect the cure, has reacted.

Approximately 60 to 80% of the Si-H groups have reacted in the composition which was fully cured. Results for dibenzofulvene are presented in Table I.

TABLE I

Increase in Uvescence in Curable Silicone containing Dibenzofulvene.

| Time[a] (min) | % SiH reacted[b] | Uvescence intensity at 318 nm (arbitrary units) |
|---|---|---|
| 0 | 0 | 3 |
| 1 | 29 | 10 |
| 2 | 31 | 10 |
| 4 | 45 | 17 |
| 6 | 52 | 23 |
| 8 | 53 | 28 |
| 10 | 57 | 33 |
| 15 | 61 | 43 |
| 20 | 63 | 82 |
| 30 | 65 | 34 |
| 60 | 67 | 25 |

[a]Time at 100° C.

[b]Percent Si—H reacted at any time t is calculated as follows, where $A^\cdot$ = absorbance of the band at 2170 cm$^{-1}$ at time zero (before the sample has been heated); $A_t$ = the absorbance at 2170 cm$^{-1}$ at time t; $B^\cdot$ = the absorbance of the band at 1950 cm$^{-1}$ at time 0 (which serves as an internal standard); and $B_t$ = the absorbance at 1950 cm$^{-1}$ at time t. Then % Si—H reacted at time t = $(100)[(A\cdot/B\cdot) - (A_t/B_t)]/[A\cdot/B\cdot]$ These data can be used to construct a calibration curve which shows when cure is complete as a function of uvescence intensity.

EXAMPLE 8

This example describes a curable silicone composition containing 6-methyldibenzofulvene as latent uvaphore; curing the composition; and analyzing the material to correlate extent of cure and uvescence intensity.

A sample was prepared of 5.0 g ethylenically unsaturated polysiloxane, 0.015 g maleate inhibitor, 0.048 g platinum catalyst, 0.049 g 6-methyldibenzofulvene (formula I, X=CHCH$_3$), and 0.129 g polyhydrosiloxane, as described in Example 7. The sample was then heated and monitored as in Example 7. Results are presented in Table II.

TABLE II

Increase in Uvescence in Curable Silicone containing 6-Methyldibenzofulvene.

| Time[a] (min) | % SiH reacted | Uvescence intensity (arbitrary units) |
|---|---|---|
| 0 | 0 | 3[b] |
| 2 | 32 | |
| 21 | 64 | 13 |
| 45 | 70 | 100 |
| 85 | 77 | 107 |

[a]at 100° C.

[b]estimated from other samples

Data of Table II can be used to construct a calibration curve which shows when cure is complete as a function of uvescence intensity.

EXAMPLE 9

This example describes a curable silicone composition containing 6-vinyldibenzofulvene [formula I, X=CH—CH=CH$_2$] as latent uvaphore; curing the composition; and analyzing the material to correlate extent of cure and uvescence intensity.

A sample was prepared as in Example 7 using 5.0 g of ethylenically unsaturated polysiloxane, 0.015 g of maleate inhibitor, 0.063 g of platinum catalyst, 0.051 g of 6-vinyldibenzofulvene, and 0.126 g of polyhydroxiloxane. The sample was heated and monitored as in Example 7, and results are presented in Table III.

TABLE III

Increase in Uvescence in Curable Silicone containing 6-Vinyldibenzofulvene.

| Time[a] (min) | % Si—H reacted | Uvescence intensity (arbitrary units) |
|---|---|---|
| 0 | 0 | 2 |
| 2 | 22 | |
| 10 | 39 | |
| 15 | 46 | |
| 40 | 45 | 10 |

[a]at 100° C.

Data of Table III can be used to compare uncured to cured material, using two data points.

EXAMPLE 10

This example demonstrates use of dibenzofulvene (formula I, X=CH$_2$) as an inhibitor of cure in a curable silicone composition.

Curable silicone compositions were prepared as in Example 7, except that in some samples, as indicated, the maleate inhibitor or latent uvaphore was omitted, or 9-allylfluorene (which is a uvaphore when added and which was used for purposes of comparison) was added instead of dibenzofulvene. The time to completely cure (approximately 60–80% Si-H reacted, monitored by IR) at 100° C. as well as the pot life (minimum time during which the viscosity of the composition does not noticeably increase at room temperature) are given for several samples in Table IV.

TABLE IV

Cure Rates and Pot Life for Curable Silicones containing Dibenzofulvene.

| Formulation | Time to complete cure (min at 100° C.) | Pot Life (hr at 25° C.) |
|---|---|---|
| curable silicone with inhibitor, but without dibenzofulvene | 2–3 | 8–24 |
| curable silicone with inhibitor, and with dibenzofulvene | 10–15 | >48 |
| curable silicone without inhibitor, but with dibenzofulvene | <10 | 8–24 |
| curable silicone with inhibitor, and with 9-allyfluorene | 4–6 | not measured |

Data of Table IV show that adequate pot life was achieved when dibenzofulvene (formula I, X=CH$_2$) was used in a formulation containing no added maleate inhibitor, and that cure times were somewhat faster in this case also.

EXAMPLE 11

This example demonstrates that the latent uvaphore becomes bound to a silicone as the latent uvaphore is converted to a uvaphore, and provides evidence for the chemical composition of the uvaphore. In this example, a low molecular weight hydrosiloxane was used to provide products which were readily analyzed.

To 0.5 g pentamethyldisiloxane was added 25 mg of latent fluorophore as indicated in Table V and 1 mg of bis(1,5-cyclooctadiene)Pt(0) (J. L. Spencer, *Inorg. Synth.* (1979) 19, 213). No attempt was made to exclude air or adventitious moisture from the samples. Samples were then heated at 100° C. for a total of 30 min., and formation of products was monitored by gas chromatography (hewlett Packard 5790 A series Gas Chromatograph, Hewlett Packard, Avondale, Pa.). Product identification was confirmed by comparison to authentic samples and/or gas chromatography/mass spectroscopy. Results are presented in Table V.

TABLE V

Uvaphore Characterization $$I \xrightarrow[Me_3SiOSiMe_2H]{Pt(O)} II \begin{array}{l}(a, Y = H, Z = SiMe_2OSiMe_3)\\(b, Y = SiMe_2OSiMe_3, Z = H)\\(c, Y = Z = H)\end{array}$$

$(X = CHR^2)$

| | Products[a] | | |
|---|---|---|---|
| $R^2 =$ | IIa + IIb | IIc | Relative Rate |
| H | 71 | 29 | 20 |
| Me | 36 | 64 | 4 |
| 9-allyl-fluorene[c] | 95 | 5 | >100 |

Notes
[a]Percentages of each product, as measured by gas chromatography, are reported.
[b]The experimental conditions were somewhat different than those that would be encountered in, for example, a thin film (the reaction was run in a closed vessel so that $H_2$ formed from any water present was unable to escape). However, results should be qualitatively similar, except that a smaller amount of hydrogenation product IIc would be expected in a thin film.
[c]9-allylfluorene was uvescent when added, was used in place of any added latent uvaphore, and was used for purposes of comparison.

Data of Table V show that the uvaphore is convalently bound to the silicone (products IIa and IIb), and show that the uvaphore is a substituted fluorene.

EXAMPLE 12

This example demonstrates that 6-vinyldibenzofulvene as latent uvaphore becomes bound to a silicone as the latent uvaphore is converted to a uvaphore.

A sample was prepared and heated as in Example 11, except that 6-vinyldibenzofulvene (formula I, $X=CH-CH=CH_2$) was the latent fluorophore. Products were analyzed as in Example 11, and proton NMR was additionally used. A number of isomeric products were possible; two major ones (accounting for >90% of the products) were identified as 9-Me$_3$SiOSiMe$_2$—9—(1-propenyl)fluorene and formula I ($X=CHCH_2CH_2SiMe_2OSiMe_3$). The latter product was not expected to be uvescent.

EXAMPLE 13 this example demonstrates the correlation between increase in uvescence and extent of cure and as monitored by IR.

28.3 mg of bis(1,5-cyclooctadiene)Pt(0) and 106 mg of 6-vinyldibenzofulvene (formula I, $X=CH-CH=CH_2$) were melted together under an atmosphere of nitrogen. The resulting red solid was used to prepare a curable silicone composition as follows: 34 mg of this material was added to 5.0 g of ethylenically unsaturated polysiloxane (as in Example 7) with 5 ml of methylene chloride. 0.126 g of polyhydrosiloxane (as in Example 7) was then added. A portion of the resulting solution was placed on a polypropylene film, solvent was allowed to evaporate, and a cover sheet of polypropylene was placed over the resulting liquid. Uvescence and IR were monitored as in Example 7. Results are presented in Table VI.

TABLE VI

| Increase in Uvescence in Curable Silicone with Premixed Catalyst. | | |
|---|---|---|
| Time[a] (min) | % Si—H reacted | Uvescence intensity at 318 nm (arbitrary units) |
| 0 | 0 | 0.8 |
| 1 | 39 | 1.7 |
| 2 | 58 | 1.8 |
| 4 | 71 | 2.0 |
| 10 | 71[b] | 4.5 |
| 25[c] | 71[b] | 14.7 |

Notes:
[a]time at 100° C.
[b]estimated based on previous measurements
[c]after 10 minutes at 100° C., the sample was heated to 120° C. for 15 minutes Data of Table VI show a faster cure and faster rate of growth of uvescence than the comparable data in Table III.

EXAMPLE 14

This example demonstrates the synthesis and an alternative workup procedure for dibenzofulvene (formula I, $X=CH_2$).

A mixture of 20.2 g 9-fluorenylmethyl chloroformate in 80 ml dry methylene chloride was cooled to 0° C. while stirring and a solution of 10 g triethylamine in 15 ml dry methylene chloride was added dropwise After the addition was complete the mixture was allowed to stir for two hours at 0° C. The reaction mixture was filtered through a glass frit and the solid washed with 125 ml cold, dry methylene chloride. The combined methylene chloride solution was washed three times with 125 ml of water, dried with anhydrous magnesium sulfate, filtered and evaporated to yield 12.0 g light yellow solid which was identified by proton nmr in CDCl$_3$ as dibenzofulvene.

EXAMPLE 15

This example demonstrates uvescence cure monitoring of polymerization of ethylenically unsaturated monomers using dibenzofulvene.derivatives.

A stock solution of 3.0 g 1,6-hexanediol diacrylate, 0.06 g azobis(isobutyronitrile) (AIBN), and 0.03 g dibenzofulvene (formula I, $X=CH_2$) was prepared, coated on polyvinylidene chloride-primed polyester film using a #14 wire wound bar (R&D Specialities, Webster, NY) and overlaid with polypropylene film. Strips of the layered construction were cured by exposure to a thermal gradient (60 to 150° C., approximately 7° C./cm) on a Heizbank Thermal Gradient device (Reichert Type 7841, Austria) for 5 minutes. The resulting films were analyzed by fluorescence spectroscopy (Perkin-Elmer MPF44B fluorescence spectrometer, excitation 254 nm, emission scanned from 260 to 400 nm, through the polypropylene side), and uvescence intensity at seven positions correlated to local Heizbank temperatures. Data are shown in Table VII below for three samples. After uvescence spectra were obtained, the polypropylene overlayer was removed and the coating rinsed with methyl ethyl ketone to remove uncured portions of the film. All of the coating at positions corresponding to Heizbank temperatures less than 110° C. rinsed off, leaving a solid (cured) film only in positions corresponding to Heizbank temperatures greater than or equal to 110° C., near the center of the response curve for uvescence intensity vs. cure temperature.

TABLE VII

Uvescence intensity as a function of cure temperature at constant cure time for thermal curing of ethylenically unsaturated monomers monitored using dibenzofulvene.

| Heizbank Temperature. °C. | Uvescence Intensity at 318 nm. arbitrary units | | |
|---|---|---|---|
| | Sample A | Sample B | Sample C |
| 80 | 7 | (a) | 1 |
| 100 | 10 | 5 | 5 |
| 110 | 26 | 9 | 22 |
| 120 | 49 | 47 | 38 |
| 130 | 80 | 62 | 67 |
| 140 | 94 | 79 | 92 |
| 150 | (a) | 89 | (a) |

(a) not measured

Data of Table VII can be used to construct a calibration curve which shows the temperature at which cure is effectively complete as a function of uvescence intensity.

EXAMPLE 16

This example demonstrates the inhibitor effect of dibenzofulvene for free radical polymerization.

A stock solution of 3.0 g 1,6-hexanediol diacrylate, 0.06 g AIBN, and 0.03 g dibenzofulvene (I, X=$CH_2$) was prepared. A second stock solution was also prepared but without the dibenzofulvene. 5 to 10 mg samples were subjected to Differential Scanning Calorimetry in sealed pans using a DuPont Model 9900 Thermal Analyzer (E. I. duPont de Nemours, Wilmington, Del.).

The sample without dibenzofulvene had a polymerization exotherm at 80° C., while the sample containing dibenzofulvene had a polymerization exotherm at 118° C., showing the inhibition effect of dibenzofulvene on free radical polymerization.

EXAMPLE 17

This example demonstrates cure monitoring of hydride curable silicones using dibenzofulvene.

To 1.51 g of the ethylenically unsaturated polysiloxane as used in Example 7 was added 0.0157 g dibenzofulvene (I, X=$CH_2$), in minimal chloroform (approximately 0.2 g), 1.53 g of the ethylenically unsaturated polysiloxane containing 100 ppm Pt(0) catalyst as used in Example 7, and 0.084 g of polyhydrosiloxane as used in Example 7. The mixture was coated on 25 micrometer thick polypropylene film using a #14 wire wound bar and overlaid with a second film of polypropylene. Strips of the layered construction were cured by exposure to a thermal gradient (60°14 150° C., approximately 7° C./cm) on a Heizbank Thermal Gradient (Reichert Type 7841, Austria) for 10 minutes. The resulting films were analyzed by fluorescence spectroscopy (Perkin-Elmer MPF44B fluorescence spectrometer, excitation 254 nm, emission monitored at 318 nm, through the polypropylene), and uvescence intensity was measured according to the procedure of Example 15. Data is shown in Table VIII below for three samples. After the fluorescence spectra were obtained, the polypropylene overlayer was removed and the film was tested for cure by rubbing with a finger. The coating was solid, non-greasy, and did not crumble where the strip had been exposed to temperatures greater than or equal to 120° C.

TABLE VIII

Uvescence intensity as a function of cure temperature at constant cure time for thermal curing of hydride curable silicones monitored using dibenzofulvene

| Heizbank Temperature. °C. | Uvescence Intensity at 318 nm. arbitrary units | | |
|---|---|---|---|
| | Sample A | Sample B | Sample C |
| 70 | 36 | 31 | 46 |
| 80 | 42 | 55 | 59 |
| 90 | 66 | 77 | 106 |
| 100 | 88 | 77 | 152 |
| 110 | 176 | 169 | 239 |
| 120 | 471 | 316 | 423 |
| 130 | 507 | 454 | 547 |
| 140 | (a) | 626 | 672 |

(a) not measured

Data of Table VIII can be used to construct a calibration curve which shows the temperature at which cure is complete as a function of uvescence intensity.

EXAMPLE 18

This example describes cure monitoring at variable temperatures of hydride curable silicones containing 9-fluorenone [I, X=oxygen].

A sample was prepared of 5.00 g ethylenically unsaturated polysiloxane, 0.053 g 9-fluorenone (dissolved with slight warming), 0.013 g maleate inhibitor, 0.052 g Pt(O) catalyst, and 0.13 g polyhydrosiloxane, as described in Example 7. 9-fluorenone is commercially available, e.g., from Aldrich Chemical Co. The sample was coated and heated on a Heizbank Thermal Gradient for 10 minutes, as described in Example 17. Using the IR absorption method described in Example 7, the extent of disappearance of Si-H bonds was measured. Data are shown in Table IX, below:

TABLE IX

Uvescence Intensity as a function of cure temperature for thermally cured silicones containing 9-Fluorenone.

| Heizbank Temperature (°C.) | % Si—H reacted[a] | Uvescence Intensity (arbitrary units) | |
|---|---|---|---|
| | | 328 nm | 355 nm |
| 70 | 51 | 62 | 90 |
| 80 | 57 | 138 | 191 |
| 90 | 63 | 205 | 296 |
| 100 | (b) | 217 | 327 |
| 110 | 57 | 401 | 621 |
| 120 | (b) | 580 | 962 |
| 130 | 65 | 465 | 764 |

[a] assuming a value at t = 0 for A·/B· of 4.0, for the calculation described in Table I, Example 7.
[b] poor quality IR spectra precluded measurement.

Data of Table IX show that when 9-fluorenone is used as latent uvaphore, uvescence intensity increases by a factor of at least 3 at the temperature where the curable silicone is fully cured, and by a factor of 10 or ore at somewhat higher temperatures.

Various modifications and alterations of this invention will become apparent to those skilled in the art without departing from the scope and spirit of this invention, and it should be understood that this invention is not to be unduly limited to the illustrative embodiments set forth herein.

We claim:

1. An article comprising a support and having applied to at least one surface thereof a curable composition consisting essentially of at least one of (a) a hydride curable silicone comprising an ethylenically unsaturated siloxane and a polyhydrosiloxane, (b) an ethylenically unsaturated compound selected from the group consisting of acrylates and methacrylates, unsaturated amides, and vinyl compounds, and (c) a cationically polymerizable monomer which is different from component (b) and is selected from the group consisting of 1,2-, 1,3-, and 1,4-cyclic ethers, vinyl ethers, N-vinyl compounds, ethylenically unsaturated hydrocarbons, cyclic formals an cyclic organosiloxanes; and dibenzofulyene or derivative thereof as a latent uvaphore which is capable of reacting during curing to form a uvaphore, said dibenzofulvene or derivative thereof having the formula

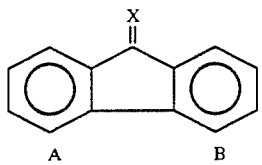

I wherein X is $CR^1R^2$ or $NR^1$, wherein $R^1$ and $R^2$ each independently is a hydrogen atom, or an alkyl, aryl, alkenyl, aralkenyl, alkynyl, aralkynyl, alkaryl, or aralkyl group, or $R^1$ and $R^2$ together are a cycloaliphatic group of ring size 3 to 12 atoms, all of which can include up to 50 carbon atoms and 0 to 30 heteroatoms selected from the group consisting of unitary N, Si, S and nonperoxidic O; and wherein aromatic groups designated A and B together or each independently contain up to two ring nitrogen atoms, and together or independently are a single or fused aromatic ring system having 1 to 4 rings.

2. The article according to claim 1 wherein the aromatic groups designated A and B of formula I are substituted by 1 to 4 substituents chosen from (1) alkyl, aryl, aralkyl, alkaryl, acylamido, acyl, amino, alkoxycarbonyl, alkoxy, aryloxy, and hydroxycarbonyl groups of up to 50 carbon atoms and 0 to 30 unitary fluoro, chloro, bromo, nitrogen, silicon, sulfur, and nonperoxidic oxygen atoms, (2) cyano, chloro, bromo, fluoro groups, and (3) silyl and siloxy groups containing up to 200 silicon atoms and up to 200 unitary nitrogen, sulfur and nonperoxidic oxygen atoms.

3. The article according to claim 1 wherein said dibenzofulvene or derivative thereof of said curable composition is selected from the group consisting of dibenzofulvene, methyldibenzofulvene vinyldibenzofulvene.

4. The article according to claim 1 wherein said dibenzofulvene or derivative thereof of said curable composition is present int he range of 0.001 to 10 weight percent of the solids content of the curable composition.

5. The article according to claim 1 wherein said curable composition consists essentially of a hydride curable silicone comprising an ethylenically unsaturated siloxane and a polyhydrosiloxane.

6. The article according to claim 1 wherein said curable composition consists essentially of an ethylenically unsaturated compound selected form the group consisting of acrylates and methacrylates, unsaturated amides, and vinyl compounds.

7. The article according to claim 1 wherein said curable composition consists essentially of a cationically polymerizable monomer which is selected from the group consisting of 1,2-, 1,3-, and 1,4-cyclic ethers, vinyl ethers, N-vinyl compounds, ethylenically unsaturated hydrocarbons, cyclic formals, and cyclic organosiloxanes.

8. The article according to claim 1 wherein said curable composition further consists of an effective amount of a thermally or photochemically activated catalyst.

9. The article according to claim 1 wherein said curable composition further consists of an inhibitor.

10. The article according to claim 1 wherein said curable composition further consists of at least one adjuvant selected from the group consisting of fillers, plasticizers, flowing agents, colorants, and pigments.

11. The article according to claim 1 wherein said support is a woven or nonwoven web.

12. The article according to claim 1 wherein said support is a solid material.

13. The article according to claim 1 which has been cured.

14. The article according to claim 13 wherein said support is a woven or nonwoven web.

15. The article according to claim 13 wherein said support is a solid material.

16. The article according to claim 13 wherein said uvaphore has the formula

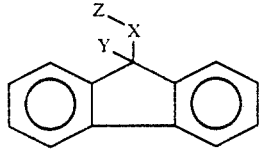

wherein X is as previously defined, and
Y and Z are chain atoms in the backbone of said cured composition.

* * * * *

UNITED STATES PATENT AND TRADEMARK OFFICE
CERTIFICATE OF CORRECTION

PATENT NO. : 5,118,559

DATED : June 2, 1992

INVENTOR(S) : Robert J. DeVoe et al.

Page 1 of 5

It is certified that error appears in the above-identified patent and that said Letters Patent is hereby corrected as shown below:

On the Cover Sheet, under [56] U.S. Patent Documents, add -- 5,037,763  08/1991  Petisce  436/172 --.

Col. 2, line 10, after "cure", insert -- of compositions such as hydride curable silicones, ethylenically unsaturated compounds, and cationically polymerizable compounds, incorporating a latent uvaphore that is converted during cure to a uvaphore, which can be used on-line, and which can be polymer-bound, thereby obviating environmental and measurement problems of "bloom". In another aspect of the invention, the latent uvaphore can additionally function as an inhibitor for certain polymerization catalysts, preventing polymerization from occurring until desired.

Briefly, the present invention provides a curable composition, the cure of which can be monitored optically in the UV, comprising at least one of a hydride curable silicone, an ethylenically unsaturated compound, and a cationically polymerizable monomer, and as cure monitor dibenzofulvene or derivatives thereof. The cure monitor is a latent uvaphore which reacts under cure conditions to form a uvaphore which preferably is polymer-bound.

UNITED STATES PATENT AND TRADEMARK OFFICE
CERTIFICATE OF CORRECTION

PATENT NO. : 5,118,559

DATED : June 2, 1992

INVENTOR(S) : Robert J. DeVoe et al.

It is certified that error appears in the above-identified patent and that said Letters Patent is hereby corrected as shown below:

In another aspect, the invention provides a method for measuring degree of cure of a polymeric material comprising the steps of:

(a) polymerizing a mixture comprising a polymerizable composition comprising at least one of a hydride curable silicone, an ethylenically unsaturated monomer or oligomer, and a cationically polymerizable monomer or oligomer, optionally a polymerization promoter, optionally a solvent, and a spectroscopically detectable amount of a latent uvaphore comprising at least one of dibenzofulvene and dibenzofulvene derivatives, in the presence of added energy when required, to provide an at least partially polymerized composition comprising a uvaphore that absorbs radiant energy of a wavelength centered around $\lambda_1$, and emits radiant energy of a wavelength centered around $\lambda_2$, $\lambda_1$ and $\lambda_2$ each being a wavelength in the ultraviolet portion of the electromagnetic spectrum, and the mean of the range of $\lambda_1$ being below the mean of the range of $\lambda_2$, --.

Col. 2, line 17, delete "$8O_2$" and insert -- $\lambda_2$ --.

UNITED STATES PATENT AND TRADEMARK OFFICE
CERTIFICATE OF CORRECTION

PATENT NO. : 5,118,559  Page 3 of 5
DATED : June 2, 1992
INVENTOR(S) : Robert J. DeVoe et al.

It is certified that error appears in the above-identified patent and that said Letters Patent is hereby corrected as shown below:

Col. 3, line 54, starting with the phrase "of composition" delete all text up to and including "$\lambda_2$" in col. 4, line 26.

Col. 10, line 68, "$[(CH_2=CH)(CH_3)SiO]_3$" should read -- $[(CH_2=CH)(CH_3)SiO]_w$ --.

Col. 11, line 9, "$[HSi(CH_3)_2O_0.59$" should read -- $[HSi(CH_3)_2O_{0.5}]$ --.

Col. 11, line 10, "$(CH_3)_3SiO[Si(CH_3)(H)Si(CH_3)_3$" should read -- $(CH_3)_3SiO[Si(CH_3)(H)O]_{35}Si(CH_3)_3$ --.

Col. 11, lines 64-65, "3,4-epoxycyclohexylmethyl3,4-epoxycyclohexanecarboxylate" should read -- 3,4-epoxycyclohexylmethyl-3,4-epoxycyclohexanecarboxylate --.

Col. 12, line 42, "such-as" should read -- such as --.

Col. 14, line 47, "formula" should read -- [formula --.

Col. 14, line 49, delete "TM" and insert therefor -- = --.

Col. 15, line 35, "7.3 x $10^6$ M" should read -- 7.3 x $10^{-6}$ M --.

Col. 15, lines 38-39, "$HSi(M-SiMe_2-OiMe_2H$" should read -- $HSi(Me)_2-O(SiMe_2-O)_{24.2}-SiMe_2H$ --.

UNITED STATES PATENT AND TRADEMARK OFFICE
CERTIFICATE OF CORRECTION

PATENT NO. : 5,118,559
DATED : June 2, 1992
INVENTOR(S) : Robert J. DeVoe et al.

It is certified that error appears in the above-identified patent and that said Letters Patent is hereby corrected as shown below:

Col. 15, lines 39-40, "8 x $10^4$ M" should read -- 8 x $10^{-4}$ M --.

Col. 16, lines 23-24, "XTMCH$_2$)" should read -- x = CH$_2$ --.

Col. 16, lines 43-44, "(CH$_2$=CH)Me$_2$Si(OSiMeOSiMe$_2$(CH=CH$_2$)" should read -- (CH$_2$=CH)Me$_2$Si(OSiMe$_2$)$_{135}$OSiMe$_2$(CH=CH$_2$) --.

Col. 16, lines 49-50, "Me$_3$SiOSiMe(H)OSiMe$_3$" should read -- Me$_3$SiO(SiMe(H)O)$_{35}$SiMe$_3$ --.

Col. 16, line 50, "(Dow Corning DC-1107™" should be followed by -- . --

Col. 17, line 59, "]formula I," should be -- [formula I, --.

Col. 17, lines 66-67, "polyhydroxiloxane" should read -- polyhydrosiloxane --.

Col. 18, line 68, "hewlett" should read -- Hewlett --.

Col. 19, lines 39-40, "9-Me$_3$SiOSiMe$_2$-9-(1-propenyl)fluorene" should read -- 9-(Me$_3$SiOSiMe$_2$)-9-(1-propenyl)fluorene --.

Col. 20, line 26, after "dropwise" insert -- . --.

Col. 22, line 57, "ore" should read -- more --.

UNITED STATES PATENT AND TRADEMARK OFFICE
CERTIFICATE OF CORRECTION

PATENT NO. : 5,118,559
DATED : June 2, 1992
INVENTOR(S) : Robert J. DeVoe et al.

It is certified that error appears in the above-identified patent and that said Letters Patent is hereby corrected as shown below:

Col. 23, lines 10-11, "debenzofulyene" should read -- dibenzofulvene --.

Col. 23, line 44, insert -- , -- after "sulfur".

Col. 23, line 49, insert -- and -- between "methyldibenzofulvene" and "vinyldibenzofulvene".

Col. 24, line 1, "int he" should read -- in the --.

Signed and Sealed this

Twenty-sixth Day of October, 1993

Attest:

BRUCE LEHMAN

Attesting Officer

Commissioner of Patents and Trademarks